United States Patent [19]

Froning

[11] 3,964,480
[45] June 22, 1976

[54] APPARATUS FOR STEROTAXIC LATERAL EXTRADURAL DISC PUNCTURE

[76] Inventor: Edward C. Froning, 215 N. San Mateo Drive, San Mateo, Calif. 94401

[22] Filed: Apr. 21, 1975

[21] Appl. No.: 569,867

Related U.S. Application Data

[63] Continuation-in-part of Ser. No. 511,655, Oct. 3, 1974.

[52] U.S. Cl............................. 128/215; 128/303 B
[51] Int. Cl.².................... A61M 5/00; A61B 17/00
[58] Field of Search................ 128/214, 214.2, 215, 128/303 B, 214.4, 2 B, 20, 329, 347, DIG. 26

[56] References Cited
OTHER PUBLICATIONS

Kendall–The Lancet, Feb. 27, 1960.
Ray–The Journal of Bone & Joint Surgery, vol. 35-A, No. 3, July 1953.
Nadvornik et al., Contin. neurol., 34: 311–314 (1972).

*Primary Examiner*—Lawrence W. Trapp
*Attorney, Agent, or Firm*—Julian Caplan

[57] ABSTRACT

A stereotaxic fixture comprises a cannula angle guide attached to an offset index, a parallel heading guide with intercept chain attached, and a frame which provides fixation for the guides, allowing rapid and secure position readjustment, and which provides retention of orientation between the guides and the lumbar spine of the patient. The cannula angle guide, offset index, and parallel heading guide adjust for depth of each individual disc, identify optimum skin puncture site, and coordinate three planes of cannula passage, providing a safe stereotaxic control of unobstructed puncture of the nucleus pulposus, for injection into the intervertebral disc of radiographic contrast fluids for diagnosis, insertion of diagnostic probes, and for injection of drugs, in particular, chymopapain, to decompress the discs by dissolving nucleus mucoproteins to relieve herniated nucleus pulposus. (See U.S. Pat. No. 3,320,131). The improvement resides in improved means for adjustably assembling the offset index relative to the heading guide support and the offset index relative to the cannula angle guide and also the provision of sleeves of a material such as paper to gauge the position of the cannula guide and depth of penetration of needles into the patient relative to the cannula angle guide.

9 Claims, 9 Drawing Figures

3,964,480

APPARATUS FOR STEROTAXIC LATERAL EXTRADURAL DISC PUNCTURE

This application is a continuation-in-part of copending application Ser. No. 511,655, filed Oct. 3, 1974.

This invention relates to a new and improved apparatus for stereotaxic lateral extradural lumbar disc puncture with features which protect the nerve root crossing over the surface of the disc in the target area of this approach.

More particularly, the invention comprises apparatus assisting the surgeon in locating cannulas for lateral disc puncture for accomplishing the operation of chemonucleolysis. In this operation, diagnostic radiographic contrast fluids are injected into the nucleus pulposus, as well as a fluid containing the enzyme chymopapain, which, when injected into the nucleus pulposus, decompresses the disc, as discovered by Dr. Lyman Smith as set forth in U.S. Pat. No. 3,320,131.

A principal advantage of the invention is provision of means to pass the cannula at approximately 45° off the midsaggital plane, an ideal approach since it is likely to clear the facet joint projection on a heading parallel to the vertebral end plates outlining the disc space, sufficiently to gain direct access to the disc center and still clearing the projecting facet joint. The present invention provides apparatus which, when used with conventional radiograpahic equipment, assists the surgeon in the safe passage of needles for puncturing of the discs at an approach which is more likely to avoid contact with the nerve roots crossing the target area of lateral extra-canal approach.

Further, the present invention provides a guidance system for all three planes of passage at an approach 45° off the midsaggital plane, providing depth control as well as a heading directly parallel to the vertebral end plates adjacent to each disc and directly over the prominence of the facet joint, presenting a suitable barrier to a medial passage of the needle which might enter the spinal canal and puncture the dural sac.

A feature of this invention is that use of the apparatus allows touching of the nerve root in a gentle enough manner to avoid injury to the nerve root during disc approach and, by permitting the patient to reveal the sensations of paresthesias produced by this nerve touching, to accurately guide the surgeon in maneuvering the docking cannula around the nerve root, permitting isolation of the nerve root, and avoiding damage thereto during disc puncture.

One of the features of the invention is the fact that the patient rests on his side on the operating table in a comfortable position. The position is also convenient from a surgeon's standpoint in adjusting the apparatus and inserting the needles.

Another feature of the invention is the saving of operation time. All of the discs may be punctured before the rotation of the C-arm of the x-ray equipment to the horizontal projection is made.

Another feature of the present invention is that the depth of disc puncture may be accurately controlled, thereby preventing under or over puncture of the nucleus.

Another feature of the invention is the control of the angle of lateral approach and adjustment to the actual depth of the disc from the skin surface as it varies from patient to patient and one disc to the other in the same patient.

Another feature of the invention is that it provides visual sighting to a precise parallel heading with the disc vertebral borders as confirmed by radiographic image.

A further feature of the invention is the provision of improved means facilitating assembly and adjustment of various members of the frame relative to each other. A clip is provided at either end of the malleable bridge consisting of a bend in the bridge lined with a material such as rubber, sponge or plastic. The vertical arm of the right angle frame slides in the clip and may be adjusted both horizontally and vertically rapidly and easily. A bridge clip is slidable in the malleable bridge, the bridge clip being movable from position to position depending upon the particular vertebral disc to be punctured. Further, the clip receives the vertical offset stem of the cannula angle guide so as conveniently and rapidly to adjust the elevation thereof.

A still further feature of the invention is the fact that the structure hereinafter described places the cannula angle guide in close proximity to the skin surface at the site of skin puncture; and further, conforms to the curvature of the back of the patient so as more accurately to locate the cannula angle guide at the exact point of needle puncture.

Another feature of the invention is the provision of sleeves of paper or other inexpensive material printed with different dimensional markings preferably in different colors. One such sleeve is used to position the cannula guide relative to the mid-sagittal plane of the patient a distance determined by pre-operative radiology. The sleeve is cut to proper length and slipped over the arm of the cannula guide. The upper end of the sleeve contacts the angle guide and the lower end has a reference marking which is brought level with one or more markings on the mid-sagittal plane of the patient by moving the arm of the cannula guide upward and downward until said reference marking is at the same level as reference markings applied to the skin of the patient at the mid-sagittal plane. Another sleeve is used to monitor the distance of penetration of the docking cannula moving in the cannula angle guide. Since the cannula angle guide is disposed at an angle of about 45°, the markings on the penetration control sleeve are 1.414 ($\sqrt{2}$) times the lengths of those on the saggital offset sleeve. Further, the markings on the docking depth sleeve take into account the length of the cannula angle guide and the length of the cannula used. Thus, by slipping these penetration monitor sleeves over the cannula and up against the hub of the cannula, when the cannula is advanced into the patient a distance such that the lower end of the docking depth sleeve contacts the cannula angle guide, the cannula tip approaches the facet joint.

Another feature of the invention is the fact that the various components are relatively inexpensive and thus may be packaged as one or more disposable kits, presterilized and containing all of the parts necessary for performance of the operation. The availability of a disposable kit insures the cleanliness control available to and required of factory environment.

Other objects of the present invention will become more apparent upon reading the following specification and referring to the accompanying drawings in which similar characters of reference represent corresponding parts in each of the several views.

ANATOMICAL CONSIDERATIONS

Figure 1:
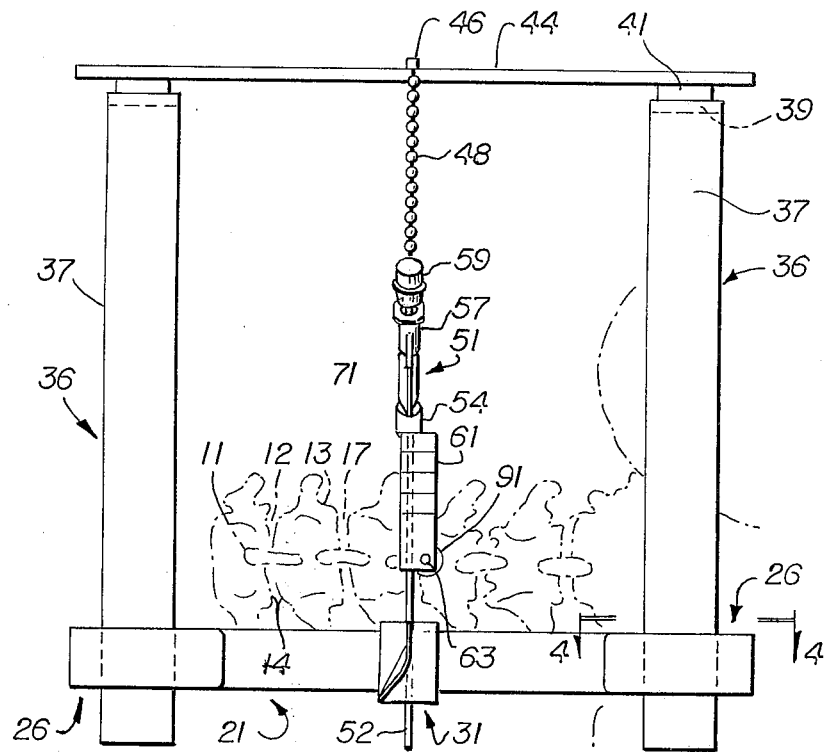
FIG. 1 is a side elevational view of one form of the invention.

The present invention is useful in treatment of the lumbar vertebrae. Each such vertebra has a spinous process 11 which projects centrally of the spine and, with the patient resting on his side, projects generally horizontally toward the surgeon. Above and below each spinous process 11 (in a radiograph) are pedicles 12 which are quite readily apparent in a radiological view and are one above the other when viewed in side elevation and are vertically aligned when viewed in top plan. The inter-vertebral discs 17 are somewhat obscured in top plan, but the dorsal profile laminar eminence 13 is readily apparent and this casts a V-shaped laminar shadow. The dorsal prominence of this V coincides with the center of the facet joint of the disc 17 and helps in docking the needle precisely lateral to the position of the pedicle 12. In docking, the end plates 14 of the vertebrae adjacent to the disc to be diagnosed and treated are used as locating means in both horizontal and vertical radiographic projection.

Pre-operative radiography is performed to determine the depth of the center of each disc 17 chosen for puncture within the body of the individual patient and measurements are made from a preliminary radiographic film made in profile with the patient lying on his side in the same position used for operation, the hips and knees half flexed and with knees and ankles separated by a pillow of appropriate thickness. The measurements are made from a radiopaque marker on the skin of the patient overlying the spinous processes.

The site of skin puncture for an angled needle approach is preferably made at an angle of 45° to the midsagittal plane of the body and this is calculated to be equidistant to the depth of the disc center from the skin surface. Appropriate calculation for the offset skin puncture distance from the mid-sagittal plane is calculated trigonometrically for variations frm the 45° angle when such variations are advantageous. The 45° angle of approach from the skin surface at the desired distance and the calculated distance from the mid-sagittal plane are least likely to coicide with the location of the nerve root crossing the postero-lateral surface of the disc and most likely to make contact with the disc surface at a location relatively comfortable to the patient, lateral to the image of the pedicle 12 and the transverse plane of the body. The optimum circumstances of the previously calculated 45° angle needle penetration approach necessitates an approach of the needle parallel to the vertebral end plates 14 of the disc junction as monitored by profile radiographic projection. This parallel heading usually coincides with the most prominent point of the curved surface of the facet joint 18. This more precise heading can be expected to avoid arteries carrying significant circulation of the spinal canal.

In performing the operation, the patient is positioned lying on his side upon a radiolucent table top, the most symptomatic side uppermost or where osseous-anomaly or overgrowth may prevent obstruction to the lateral approach to the disc, the side of least interference uppermost. The patient's torso is strapped, or retained, in a fashion so as to prevent drift out of lateral position should this occur if the patient drifts off to sleep during the semi-conscious anesthetic state preferable for this operation.

The skin is prepared by use of a routine disinfecting agent, a sterile plastic adherence sheet is placed over the skin in the operative area. Thereupon, the frame hereinafter described is attached.

Radiographic skin tabs 91 are placed over the spinous processes 11 of the vertebrae between which the discs to be punctured are located, thereby identifying the mid-sagittal plane to be used as a starting point for measuring skin puncture offset distance from the midline.

Other details of the pre-operative examination and preparation of the patient are disclosed in said application Ser. No. 511,655 as are details of the needles used and the method of performing the operation. These details are not repeated in the present application.

Apparatus — FIG. 1

Adjacent either end of horizontal malleable bridge 21 positioned below but parallel to a line on the skin coinciding with the spinous processes 11 determined by tabs 91, is end clip 26. Horizontal malleable bridge 21 is preferably formed of a readily flexible, thin metal such as aluminum. The central portion 22 thereof is bent inward to conform to the curvature of the back of the patient and slanted portions 23 at either end of the central portion have end clips 26 on their outer extremities. Each end clip 26 is formed by a reverse bend 27 of the guide 21 and an overlapping portion 28 so that clip 26 in top plan is U-shaped. The inside of clip 26 is lined with sponge rubber or a plastic equivalent thereto. Vertical arm 37 of right angle frame 36 is received between the layers of lining 29 and the same may be moved longitudinally and vertically relative to the patient. Right angle frames 36 extend adjacent each end of bridge 21 vertically up along the back of the patient. Frame 36 has a vertical arm 37 and at its upper end has a horizontal arm 39. Preferably arms 39 are level with each other. As is apparent from FIGS. 1–3, frame 36 may be moved inward and outward relative to bridge 21 and vertical arms 37 may also be moved upward and downward relative to end clips 26 so that the horizontal arms 39 are in proper position. Arms 37 are then strapped to the patient by tape or other suitable means.

Supported by horizontal arms 39 is a longitudinally extending horizontal heading guide longitudinal member 41. In the form of invention shown in FIGS. 1–3, a metallic insert 41 is imbedded in or applied to horizontal arm 39 of each heading guide 36. A pair of generally parallel, longitudinally disposed heading guide magnetic strips 44 bridge the distance between the two frames 36 and are attracted to the metallic inserts 41.

Figure 8:
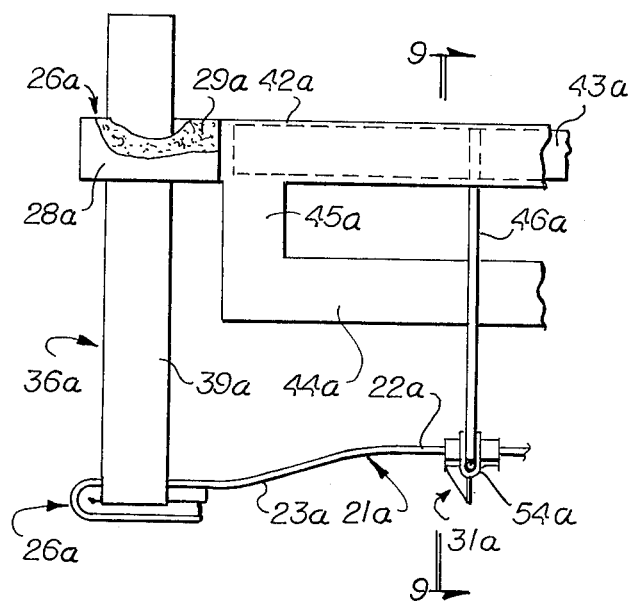
FIG. 8 is a fragmentary top plan similar to FIG. 2 of a modification.
Figure 9:
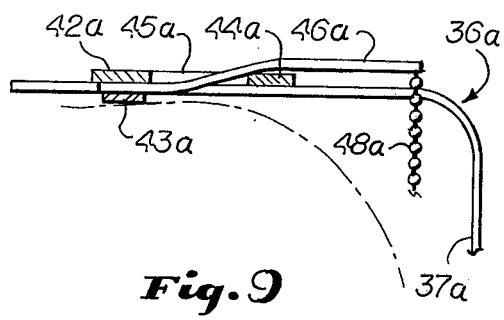
FIG. 9 is a sectional view taken along the line 9—9 of FIG. 8.

FIG. 8 Modification

In the modification shown in FIG. 8, longitudinal member 42a is formed at either end with a clip 26a similar to clip 26 heretofore described and engaging horizontal arm 39a of each support 36a. Below strip 42a for at least a portion of its length, is bottom strip 43a which is spaced slightly below strip 42 for a purpose which hereinafter appears. Spaced horizontally forward of strip 42a is forward strip 44a connected to strip 42a by legs 45a. In other respects, the form of invention shown in FIG. 8 resembles that of the preceding modification and the same reference numerals followed by the subscript a are used to designate corresponding parts.

FIG. 1 Modification Continued

Figure 2:
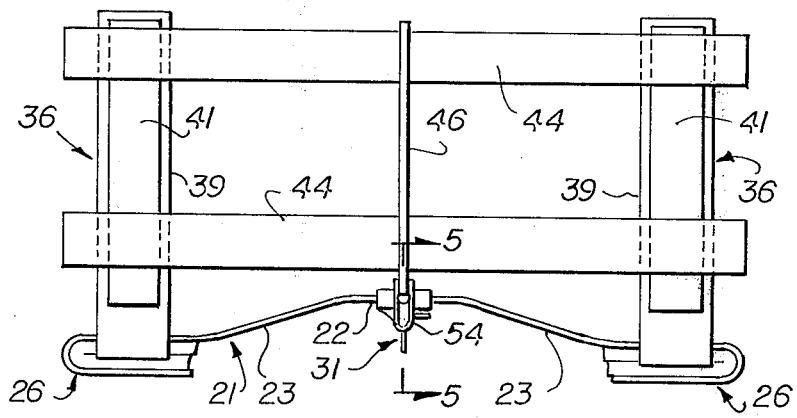
FIG. 2 is a top plan view thereof.
Figure 3:
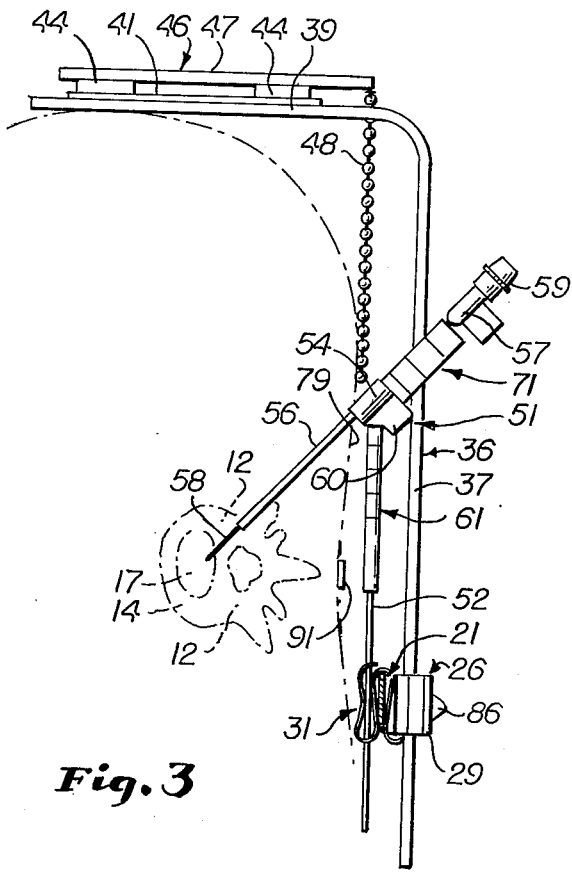
FIG. 3 is an end elevation viewed from the left of FIG. 1.
Figure 4:
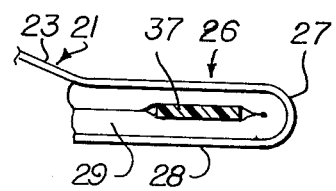
FIG. 4 is an enlarged, fragmentary sectional view taken substantially along the line 4—4 of FIG. 1.

Heading guide 46 comprises a thin, narrow, semi-radiologically opaque ferrous springdisc overlay strip and a depending intercept chain 48. The proximal end of strip 47 in the form of FIGS. 1–3 is secured by magnetic attraction to strips 44 and in the form of FIG. 8 is inserted between strips 42a and 43a and bent over the top of strip 44a. Thus the strip 47 may be moved longitudinally and also adjusted in angular position on a heading bisecting the angle between the plates 14 of the adjacent vertebrae but is held in adjusted position by friction or magnetic attraction. Chain 48 hangs by gravity and serves as a locating guide for the cannula angle guide 51 hereinafter described. By x-ray technique, the guide 46 is moved longitudinally of member 41 so that the chain 48 is positioned in alignment with each of the discs to be treated, it being understood that the guide 46 is moved serially from one disc to another as the operation proceeds.

Figure 5:
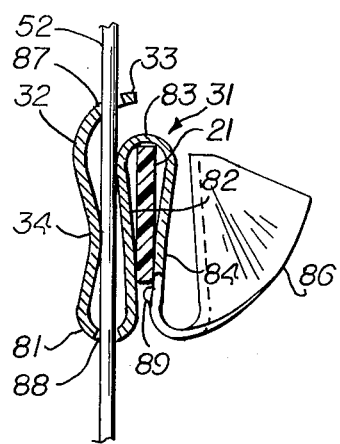
FIG. 5 is an enlarged, fragmentary sectional view taken substantially along the line 5—5 of FIG. 2.

Offset index-cannula angle guide 51 has half round channel 54 from which depends cannula offset stem 52. The angle between the channel in guide 51 and stem 52 is preferably 45°. The lower end of stem 52 is secured by bridge clip 31 which is slidable on bridge 21. Thus the clip 31 slides along bridge 21 until the guide 51 is immediately under the chain 48. Clip 31, best shown in FIG. 5, comprises a complex curved back 32 having a forwardly curved upper end 33, a forwardly curved middle portion 34 and bottom U-bend 81 which joins the central stretch 82 which extends upward relative to bend 81. At the top of stretch 82 is a second or top U-bend 83 which joins the front downward extending stretch 84 having a dimple 89 which secures bridge 21 between stretches 82 and 84 and against the underside of bend 83. At the lower end of stretch 84 is an upwardly and then forwardly twisted finger grip 86. Top aperture 87 is formed in upper curved portion 33 and bottom aperture 88 is formed in bottom U-bend 81. The stem 52 of the needle angle guide is inserted through apertures 87, 88 and is frictionally held in position by contact with curved portions 34 and 83. Portions 82 and 84 are slipped over the bridge 21. As is apparent, the clip 31 may be moved from location to location longitudinally of guide 21 by gripping the finger grip 86; and once in position, is frictionally held. Similarly, the stem 52 may be moved upward and downward relative to the clip 31 against the frictional force tending to hold the stem 52 relative to the clip. By calculations made prior to the operation, it is determined the distance which channel 54 must be positioned above spinous process 11. This distance is equal to the depth of the center of disc 17 below the skin surface as per pre-operative radiograph. Once this determination has been made, a saggital offset sleeve 61 of proper length is slipped over the stem 52 and stem 52 is slid in clip 31 so that reference marker 63 of sleeve 61 rests opposite the midline radiographically opaque tabs 91.

Figure 6:
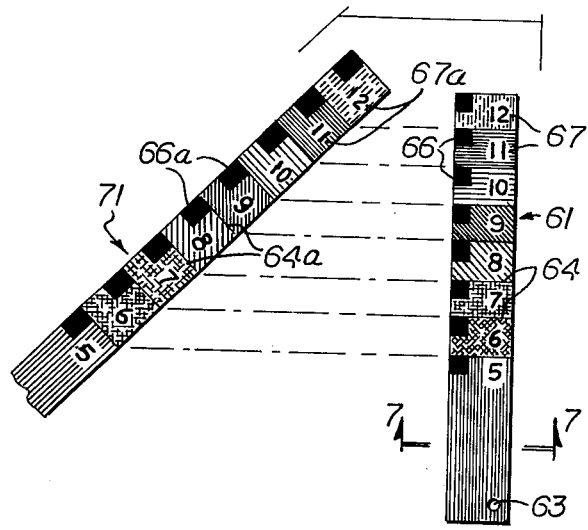
FIG. 6 is an enlarged, partially schematic, view showing the cannula guide positioning sleeve and docking depth sleeve and the dimensional relationship of the markings thereon.
Figure 7:
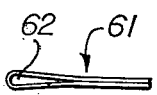
FIG. 7 is a further enlarged sectional view taken substantially along the line 7—7 of FIG. 6.

Sleeve 61, best shown in FIGS. 6 and 7, is preferably formed of an inexpensive, easily cut material such as paper. The paper or other sheet is folded over and formed with an opening 62 through which the stem 52 passes. Adjacent the lower end of sleeve 61 is a reference marker 63 which is aligned at the level of tabs 91 applied to the skin of the patient and the mid-sagittal plane as defined by the spinous processes 11. Markings 64, preferably in centimeters, are marked on the sleeve 61; and to assist in reading the markers, the spaces there-between are preferably of different colors. Further, half centimeter markings 66 may be provided. From preliminary calculations, the distance from tab 91 to the site of the skin puncture is known. The sleeve 61 is cut to the proper length and then slipped over the stem 52. By raising and lowering the angle guide 51 in the clip 31 the marker 63 is brought into level with the tab 91.

A series of cannulae and needles is slipped through the channel 54 in guide 51. Preferably a docking cannula 56 which is tubular and is formed at its outer end with a hub 57 is first used. A finger grip 60 on hub 57 assists in aligning and inserting cannula 56. Preliminary to insertion, as is shown in FIG. 3, a stylet 59 is inserted into the cannula 56 so that its tip projects slightly to penetrate skin and muscle. For accurate determination of the maximum penetration the preliminary radiological analysis has been made of the maximum distance which the tip of needle 58 may penetrate to make contact with the disc to be treated but which will not be greater than said distance so that the needle 58 or the puncturing needle (not shown) which is subsequently inserted will not injure the patient. For such purpose, a docking depth sleeve 71 similar in structure and function to sleeve 53 is installed over the docking cannula 56 in contact with hub 57. For a 45° angle approach, markings 64 on sleeve 71 have a length relationship equal to 1.414 times those of sleeve 61. The construction of sleeve 71 resembles that of sleeve 61 and the same reference numbers followed by subscript a are used to designate corresponding parts.

Heading guide 46 is preferably of a material which is semi-radiopaque or half radiopaque and half radiolucent. Thus the guide 46 shows in the radiological view but does not obscure the cannula 56 while docking against the disc while assisting the surgeon maneuver the docking cannula into place.

A radiologically opaque fluid is inserted into the nucleus propulsus. Diagnosis of whether there is rupture or herniation of the disc is made radiologically. If rupture or herniation are apparent, the enzyme is inserted.

To summarize the use of the apparatus heretofore described, preliminarily by radiograhic analysis the distance from the center of disc 17 to the skin of the patient is calculated. At the commencement of the operation, tabs 91 are applied to the surface of the torso of the patient opposite the spinous processes 11. The sleeves 61, 71 are cut to proper length. Horizontal malleable bridge 21 is fixed to the skin a proper distance below the tabs 91 overlying the erector spinae muscles, parallel to the spine. The vertical arms 37 of right angle frames 36 are inserted through the clips 26 so that the horizontal arms 39 overly the patient. Thereupon, the frames 36 are taped to the torso. The heading guide longitudinal members 41 or 41a are attached to the frames 36 either by the means shown in FIGS. 1–3 or FIG. 8. The heading guide 46 is then installed in proper longitudinal position and in a proper angle relative to the end plates 41 defining the disc 17 first to be treated. The chain 48 hangs vertically downward to a location adjacent the site of puncture and is cut to length so that it does not interfere with cannula penetration. Stem 52 is inserted in bridge clip 31 and the reference marker 63 brought into coincidence with the tab 91 on the skin. The inner end of the channel 54 is thereby in position at the skin puncture site. The docking cannula 56 and a needle 58 are selected and the proper length docking depth sleeve 71 slipped over the cannula 56 below hub 57. The needle 58 is then advanced into the skin at the site and its direction is radiologically monitored parallel to heading guide 46. In copending application Ser. No. 511,655, the specific details for inserting the needles into proper position and injecting diagnostic and therapeutic fluids is disclosed and is not repeated herein. Heading guide 46 is moved from position to position for each disc to be punctured and the needle insertion technique outlined is repeated as required.

What is claimed is:

1. Apparatus for lateral extradural disc puncture comprising a bridge adapted to be fixed in position along the back of the patient parallel to and below the spinous processes,
   at least one frame having a first stretch and a second stretch angularly related to said first stretch,
   cooperating first means on said bridge and said first stretch for adjustably positioning said frame vertically and horizontally relative to said bridge so that said second stretch overlies the patient,
   a stem,
   an cannula angle guide connecting said stem relative to said bridge to determine the position of said cannula angle guide both from the midsagittal plane of the patient and longitudinally relative to the intervertebral discs of said patient,
   a heading guide,
   cooperating third means adjustably positioning said heading guide relative to said second stretch substantially horizontally and longitudinally relative to said patient.

2. Apparatus according to claim 1 wherein said first means comprises a reverse bend in an end of said bridge and frictional material folded inside said bend, said first stretch extending inside the fold of said material and movable inside said fold both vertically and horizontally.

3. Apparatus according to claim 1 in which said bridge is formed of malleable material which is bendable to conform to the curvature of the back of said patient so that said stem is in proximity to the skin of the patient, said first means comprising a U-shaped bend in an end of said bridge, and resilient material inside said bend frictionally holding said first stretch in a desired position of adjustment.

4. Apparatus according to claim 1 in which said second means comprises a clip having a first passage to receive said stem, said clip being movable along said bridge and said clip adjacent said first passage being resiliently biased to hold said clip on said bridge against unintentional movement, said clip having a second passage to receive said stem, said stem being movable relative to said clip, said clip adjacent said second passage being resiliently biased to hold said stem relative to said clip against unintentional movement.

5. Apparatus according to claim 1 which further comprises a removable sleeve on said stem, said sleeve being severable into lengths to gauge the distance of said cannula angle guide from a reference marker on the back of the patient, said sleeve having markers indicating said lengths.

6. Apparatus according to claim 1 which further comprises a cannula through said cannula angle guide, said cannula having a hub, and a removable sleeve on said cannula, said sleeve being severable into lengths to gauge the distance of said hub from said cannula angle guide and, for a known cannula length, thereby to gauge the penetration of said cannula into the patient beyond said cannula angle guide, said sleeve having markers indicating said lengths.

7. Apparatus according to claim 6 which further comprises a removable second sleeve on said stem, said second sleeve being severable into second lengths to gauge the distance of said cannula angle guide from a reference marker on the back of the patient, said second sleeve having second markers indicating said second lengths, the ratio between said first-mentioned markers and said second markers being related to the cosine of said predetermined angle.

8. Apparatus according to claim 1 in which said third means comprises plural heading guide strips and said heading guide is frictionally held between said heading guide strips.

9. Apparatus according to claim 1 in said heading guide support is of magnetic material and said third means comprises magnetic attraction of said heading guide support to said second stretch.

* * * * *